United States Patent
Ammann et al.

(10) Patent No.: US 8,067,356 B2
(45) Date of Patent: Nov. 29, 2011

(54) HIGH FIBRE HIGH CALORIE LIQUID OR POWDERED NUTRITIONAL COMPOSITION

(75) Inventors: Christina Ammann, Bannwil (CH); Florence Rochat, Montreux (CH); Claudia Roessle, Morges (CH)

(73) Assignee: Nestec S.A., Vevey (CH)

( * ) Notice: Subject to any disclaimer, the term of this patent is extended or adjusted under 35 U.S.C. 154(b) by 1221 days.

(21) Appl. No.: 10/564,452

(22) PCT Filed: Jul. 12, 2004

(86) PCT No.: PCT/EP2004/007674
§ 371 (c)(1),
(2), (4) Date: Jan. 12, 2006

(87) PCT Pub. No.: WO2005/013721
PCT Pub. Date: Feb. 17, 2005

(65) Prior Publication Data
US 2006/0246179 A1    Nov. 2, 2006

(30) Foreign Application Priority Data
Jul. 15, 2003  (EP) .................................. 03016058

(51) Int. Cl.
*A01N 61/00*  (2006.01)
*A61K 31/00*  (2006.01)
*A23L 1/30*  (2006.01)

(52) U.S. Cl. ............. 514/1; 426/648; 426/800; 426/801

(58) Field of Classification Search ........... 426/1; 514/1
See application file for complete search history.

(56) References Cited

U.S. PATENT DOCUMENTS

| 4,833,128 A | 5/1989 | Solomon et al. |
| 6,200,950 B1 | 3/2001 | Mark et al. |
| 6,489,310 B1 * | 12/2002 | Brassart et al. .............. 514/54 |

FOREIGN PATENT DOCUMENTS

| EP | 0756828 | 11/1998 |
| EP | 0721742 | 6/2002 |
| EP | 1314362 | 2/2005 |
| WO | WO99/42001 | 8/1999 |
| WO | WO02/39834 | 5/2002 |
| WO | WO03/053165 | 6/2003 |

* cited by examiner

*Primary Examiner* — D Lawrence Tarazano
*Assistant Examiner* — Elizabeth Gwartney
(74) *Attorney, Agent, or Firm* — K&L Gates LLP

(57) ABSTRACT

The present invention relates to a nutritional composition which is liquid and shelf-stable or powdered and reconstitutable. The composition has a fiber content of more than 2.5 g/fibber per 100 ml of the composition. Furthermore, it has an energy content of 1.3-1.8 kcal/ml. The composition is useful to improve and maintain gut comfort, restoring a well-balanced gut flora, especially in an elderly patient prone to malnutrition. The invention further relates to a process for preparing the nutritional composition.

10 Claims, No Drawings

HIGH FIBRE HIGH CALORIE LIQUID OR POWDERED NUTRITIONAL COMPOSITION

The present invention relates to a nutritional composition, the use of a nutritional composition to promote gut comfort and a process for preparing the nutritional composition. Furthermore, the present invention relates to a method for providing nutrition and improving the digestive tract and bowel function and to a method for enhancing mucosal function.

THE BACKGROUND ART

The risk of malnutrition is high during innumerable circumstances of life. For example, as discussed in U.S. Pat. No. 6,200,950, metabolically stressed patients suffering from impairment of either digestion or absorption due to diseases affecting the gastrointestinal tract are prone to malnutrition. Examples of such disease are functional dyspepsia, various forms of gastritis, peptic ulcers, colitis ulcerosa, neoplasms of the stomach, pancreatitis, diarrhoea, constipation, Crohn's disease, IBS, post-operative condition after gastro-intestinal surgery, just to mention a few.

Malnutrition or gastro-intestinal disorders, more generally gut-discomfort or pain may simply be the consequence of unhealthy or unbalanced nutritional behaviour. Especially, fast food is very often rich in cholesterol, has generally an unbalanced nutritional profile and can therefore lead to malnutrition.

EP 0 721 742, for example, points out the occurrence of malnutrition with elderly people or patients and discloses a nutritional composition addressing this situation.

On the other hand, trauma or surgery patients may be in need of a high calorie and nutrient nutritional products, such as disclosed in U.S. Pat. No. 5,221,668.

However, malnutrition may also affect perfectly healthy people, be it due to increased energy expenditure, as is the case with athletes or other sportsmen following intensive physical exercise, be it in other circumstances, such as pregnancy, for example.

The occurrence of malnutrition in various situations during life, in particular with elderly or ill people has thus led mainly to high calorie and high nutrient compositions. The concept was to provide a maximum of energy and essential nutrients in a minimal volume to be consumed.

However, consumption of compositions of the state of the art was often problematic, especially in patients with unbalanced gut flora and with gut impairment. These compositions can cause gut pain or gut discomfort and are not always well supported.

It is an object of the present invention to provide a nutritional composition, which has a high energy content and which improves the digestive tract health.

It is a further object to provide a nutritional composition, for example in the form of a nutritional supplement, which improves and maintains a well-balanced gut flora and which improves intestinal transit.

It is, in particular, an object of the invention to provide a nutritional composition to regulate gut motility and/or to improve intestinal transit, also suitable for persons suffering from diarrhoea or constipation.

It is another object of the present invention to provide a nutritional composition, which has an increased fibre content, more particularly, which comprises an optimised mixture of different classes of fibre.

It is a further objective of the present invention to provide a nutritional supplement with high fibre and high energy content and which may further comprise other essential nutrients.

Another object of the present invention is to provide a product that has a specific range of fibre density, which gives excellent gut-benefits, such as well-being, gut-comfort, prevents constipation and diarrhoea and results in soft stool.

It is a further object to provide a liquid product with a good taste, and a product that is shelf stable.

SUMMARY OF THE INVENTION

Remarkably, a nutritional composition is provided, which is rich in fibre, includes different classes of dietary fibre to promote gut health and has a high energy content. Remarkably, such a composition may also be prepared, if desired, to be nutritionally complete and balanced.

In a first aspect, the present invention provides a liquid or powdered and reconstitutable nutritional composition comprising a protein source, a source of digestible carbohydrates and a source of dietary fibre, characterised in that it has an energy density of 1.4-1.8 kcal/ml and dietary fibre in an amount of more than 2.5 g/100 ml (in each case after reconstitution if appropriate).

In a second aspect, the present invention provides a method for preparing the nutritional composition according to the present invention, comprising the steps of
  mixing components of the composition, and,
  hydrating the components to provide a liquid mixture.

In a third aspect the present invention provides a method for providing nutrition and improving the digestive tract and bowel function and/or to maintaining or restoring a well-balanced gut flora comprising the step of administering to a individual the nutritional composition according to the present invention.

In a fourth aspect, the present invention provides a method for enhancing mucosal function in a human individual, comprising the step of administering to a human individual the nutritional composition according to the present invention.

DETAILED DESCRIPTION OF THE INVENTION

In the context of the present invention, the term "dietary fibre" designates carbohydrates that are not digested or absorbed in the stomach and the small intestines and thus essentially arrive at the large intestine.

The different forms of dietary fibre are divided into classes by different parameters. Hence, dietary fibre can be divided in soluble and insoluble fibre according to solubility in water, the standard protocol is found in L. Prosky et al., J. Assoc. Off. Anal. Chem. 71, 1017-1023 (1988). Examples of typically soluble fibre are inulin, pectin, β-glucans, various gums such as gum arabic, tragacanth, mucilages, guar and locust bean gum, agar, carageenans, alginates, xanthan and the like. These ingredients are commercially available.

Insoluble fibre include cellulose and others, suitable sources of insoluble dietary fibres are hull fibres from legumes and grains; for example pea hull fibre, oat hull fibre, barley hull fibre, and soy hull fibre. Pea outer fibre is identical to the term pea hull fibre.

Often, raw materials rich in fibre comprise different sorts or classes of fibre. For example, pea inner fibre, also called pea cellular walls, generally comprises (fibre only) 10-20% of cellulose, 40-50% of hemicellulose and 35-45% of pectin. Pea inner fibre may be commercially obtained under the tradename Swelite® from Cosucra, for example, a product, which further comprises starch.

Fibre may further be classified in fermentable and non-fermentable fibre, according to its ability to serve as a substrate for the colonic bacterial flora. While fermentable fibre is usually broken down to smaller molecules, such as short chain fatty acids, non-fermentable fibre cannot or only hardly be broken down by the micro-organisms in the human colon and therefore essentially appears in stool.

Furthermore, carbohydrates and hence most of all fibre is widely classified according to degree of polymerisation (DP) of the monosacharide units constituting a single fibre-molecule. For the purpose of the present invention, oligosaccharides are defined as having a DP of 3 to 10, while polysaccharides cover all carbohydrates having a higher DP. Oligosaccharides may thus be a mixture of saccharides of a specific structure but of varying DP, but of which more than 50% by weight of all of the saccharides have a DP in the range of 3-10. FOS, for example, are commercially obtainable in the form of such a mixture.

Examples of oligosaccharides include fructo-oligosaccharides (FOS), which may be obtained by hydrolysis of inulin or by synthesis from sucrose by action of fungal β-fructofuranosidase. Other oligosaccharides are lacto-oligosaccharides, galacto-oligosaccharides, xylo-oligosaccharides, gluco-oligosaccharides, for example.

The structure of a specific fibre, which usually determines its denomination, depends on the kind, order and quantity of specific monosaccharide units as well as the kind of linkage between the monosaccharide units.

Since also starch is not always totally degraded in the small intestines (="resistant starch") the term "non-starch polysaccharides" is generally used to clarify that carbohydrate-fibre different from starch is meant.

The term digestible carbohydrates, in the context of the present invention, refers to sugars, starches and other carbohydrates that are broken down by enzymes in the small intestines to absorbable monosaccharides.

All percentages refer to percent by weight, unless otherwise indicated.

Preferably, the composition according to the present invention comprises different classes of fibre, and/or fibre of different structure.

In an embodiment of the present invention, the source of fibre of the nutritional composition according to the present invention is selected from the group of soluble non-starch polysaccharides, insoluble non-starch polysaccharides, oligosaccharides, and mixtures of these.

In a further embodiment of the present invention, the source of dietary fibre of the composition comprises, in percent by weight of total fibre, 20-40% of soluble non-starch polysaccharides, 30-60% of insoluble non-starch polysaccharides, and 20-40% of oligosaccharides. Preferably, the composition comprises, in increasing amounts, insoluble non-starch polysaccharides, soluble non-starch-polysaccharides and oligosaccharides.

More preferably, the source of dietary fibre comprises, in percent by weight of total fibre 25-35%, for example 30%, by weight of soluble non-starch polysaccharides, 37-47%, for example 42%, by weight of insoluble non-starch polysaccharides, and 25-35%, for example 30%, by weight of oligosaccharides.

Preferably, the composition according to the present invention, if liquid or powdered and reconstituted in water preferably comprises more than 2.4 g, 2.45 g, 2.5 g, 2.55 g, or 2.6 g more preferably more than 2.65 g, for example 2.7 g or more of dietary fibre per 100 ml.

For example, the composition according to the present invention comprises 2.5-3.3 g dietary fibre per 100 ml, preferably 2.55-3 g per 100 ml, most preferably 2.6-2.9 g dietary fibre per 100 ml.

Preferably, the composition according to the present invention, provides, expressed in weight of dietary fibre per serving size of 200 ml, 1-2 g, preferably 1.3-1.8 g, of soluble non-starch polysaccharide per 200 ml, 1-2 g, preferably 1.3-1.8 g, of oligosaccharides per 200 ml and 1.5-3 g, and/or preferably 2-2.5 g of insoluble non-starch polysaccharides per 200 ml of the composition according to the present invention.

Preferably, the ratio of soluble fibre, including oligosaccharides, if present, to insoluble fibre is in the range of 0.8-2, more preferably 1-1.8, most preferably 1.3-1.7.

The composition according to the present invention may comprise any suitable source of dietary fibre, such as soluble and insoluble non-starch polysaccharides and/or oligosaccharides known to the skilled person or mentioned above.

However, in an embodiment of the composition according to the present invention, the source of soluble non-starch polysaccharide is acacia gum, the source of insoluble non-starch polysaccharides is pea outer fibre and the oligosaccharides are fructo-oligosaccharides.

Pea outer fibre (pea hull fibre) is commercially available under the tradenames Exafine® of Cosucra or Sofalite®D of Sofalia in Puteaux, France. Pea outer fibre may be obtained from Yellow Pea (*Pisum sativum*) and generally comprises 65-70% of cellulose, 22-28% of hemicellulose and about 5-10% of lignin.

The composition according the present invention comprises at least one source of digestible carbohydrates. The digestible carbohydrate source may be any suitable carbohydrate or carbohydrate mixtures. For example, the carbohydrate source may be maltodextrin, native or modified starch from tapioca, corn, rice, other cereals, potato, for example, or high amylase starch, sucrose, glucose, fructose, and/or mixtures thereof. Preferably, the digestible carbohydrate source comprises maltodextrin and sucrose. If the carbohydrate source includes maltodextrin, maltodextrin with a DE (Dextrose Equivalent) of between 10 and 40, preferably 15-30, more preferably 21-23 is preferred.

In an embodiment of the present invention, the composition is clinically free of lactose. The term "clinically free of lactose" refers, in the context of the present invention, to nutritional compositions that have a maximum of 0.2 g lactose per 100 kcal of the composition. Preferably, the composition has less than 0.2, more preferably less than 0.17 g lactose per 100 kcal of the composition.

The digestible carbohydrate source, may provide provides 35% to 65% of the energy of the composition; preferably 40% to about 60%, more preferably 45 to 55%, most preferably 48 to 54% of the energy. For example, the carbohydrate source may provide about 50% of the energy of the composition.

The nutritional composition according the present invention comprises a protein source, which may be selected from any protein source useful as ingredient in nutritional compositions. Preferably, a high quality protein source is used; for example milk protein, whey, casein, or soy protein, or mixtures of these proteins. The protein source may be in the form of intact protein or may be hydrolysed. Other protein sources such as rice, pea and oat protein, or mixtures thereof, may also be used. Further, if desired, the protein source may include free amino acids. Preferably, the protein source comprises caseinates, such as sodium and/or potassium caseinate and/or milk protein concentrates.

If the composition according to the invention is a liquid composition, it comprises, in an embodiment, 4.5 to 6 g protein/100 ml. Preferably, the composition comprises 5.2-5.8 g protein/100 ml, more preferably 5.4-5.7 g protein/100 ml.

The protein source may provide about 8% to about 20% of the energy of the composition. Preferably, the protein source provides about 11% to about 19% of the energy of the composition. More preferably, it provides 13 to about 17%, for example about 15% of the energy of the composition.

In an embodiment of the present invention, the composition further comprises a source of lipids. Sources of lipids for use in nutritional compositions may be selected from olive oil, sunflower oil rich in oleic acid, (low erucic) rapeseed oil rich in oleic acid, hazelnut oil, safflower oil, soy oil, corn oil, coconut oil, milk fat, black currant seed oil, fish oil, palm oil, peanut oil, and mixtures of these, for example. Preferably, the lipid source is selected from soy oil, milk fat, low erucic rapeseed oil, corn oil, and mixtures of these.

Preferably, the composition has a n-6/n3-ratio in the range of 4 to 12, more preferably 5-10, most preferably 7-8.

The lipid source may comprise saturated fatty acids (SFA), monounsaturated fatty acids (MUFA), and/or polyunsaturated fatty acids (PUFA). SFA may partially be present as medium chain triglycerides (MCT), MCT referring to triglycerides comprising $C_6$-$C_{12}$ fatty acids.

Preferably, the lipid source comprises SFA, MUFA, PUFA in increasing quantities. Preferably, in percent by weight of the lipid source, the composition comprises 10-15% of SFA, 30-50% MUFA, 35-55% PUFA.

The lipid source may provide 25-45% of the energy of the composition. Preferably, the lipid source provides 30-40%, more preferably 32-38% of the energy of the composition.

Preferably, the composition comprises less than 1 mg, more preferably less than 0.5 mg of cholesterol per 100 ml.

Food grade emulsifiers may be added as required.

The composition preferably includes a complete vitamin and mineral profile. For example, sufficient vitamins and minerals may be provided to supply about 75% to about 250% of the recommended daily allowance of the vitamins and minerals per 1000 calories of the nutritional composition. These values may be adjusted in case the nutritional composition is not the sole nutrition. Some minerals and vitamins, such as Mg and Zn may be added in lower concentrations.

The composition according to the present invention has an energy content of 1.3-1.8 kcal/ml. Preferably, it has an energy content of 1.4-1.6 kcal/ml.

In a preferred embodiment, the nutritional composition according to the present invention is non-GMO. The term "non-GMO" means that the origin of a product (all the raw materials) do not contain GMOs. However, small traces of genetically modified organisms may be found in a product, which may be due to contamination of raw materials during transport for example. More precisely "non-GMO" means that up to 0.9 wt. % of dry matter of the product according to the invention may be or contain a GMO.

More preferably, the nutritional composition according to the present invention is free of GMOs, in other words, no detectable trace of a GMO may be found in the product with any known method.

For example, the nutritional composition according to the present invention comprises a protein source, a lipid source and a source of digestible carbohydrates, the protein source providing 10-20%, the lipid source providing 30-40% and the digestible carbohydrate source providing 45-55% of the total energy of the composition. More preferably, these sources provide 12-17, 32-37, and 47-53% of the energy of the composition, respectively.

In an embodiment, the composition according to the present invention has a viscosity of 30-80 mPas. Preferably, viscosity is measured with an HAAKE RS100 apparatus at 20° C. and a shear rate of 0-300s$^{-1}$.

The nutritional composition of the present invention may be a liquid, shelf-stable, or a powdered, reconstitutable composition. If it is a liquid composition, it is preferably provided in cups, bottles, tetra or Combibloc packs or other containers of a serving volume of about 150-400 ml, more preferably 180-300 ml, for example 200-250 ml.

Preferably, the composition according to the invention is a shelf stable, liquid and ready-to-use composition. It preferably has a shelf life of at least 4 months, preferably 5 to 13 months, more preferably 7-12 months at room temperature.

If the composition is a liquid, shelf-stable composition, it is preferably shaken slightly shortly before consumption, to redistribute possibly sedimented or settled insoluble components, such as certain fibre.

If the composition is a powdered formula, it is preferably reconstituted with water, such as nutritionally safe tap water or filtered water.

The nutritional composition may conveniently have an osmolality of about 350-670 mosm/kg $H_2O$, preferably of 500-650 mosm/kg $H_2O$, more preferably of 570-640 mosm/kg $H_2O$.

Preferably, the nutritional composition has an osmolarity 400-500 mosm/L.

The nutritional composition according to the present invention is rich in fibre, that is, it comprises more than 5 g fibre per serving. It is useful to improve and maintain a well-balanced gut flora. Furthermore, it is suitable to improve intestinal transit, to alleviate constipation and/or diarrhoea. The composition according to the present invention is thus suitable to treat or prevent gut pain and to support gut comfort.

Preferably, the present invention provides a composition for use as prophylactic and/or treatment nutrition. In particular, the nutritional composition supports recovering and/or healing from disease or malnutrition.

In a further embodiment, the composition for provides nutrition and improves the digestive tract and bowel function and/or to maintains or restores a well-balanced gut flora.

In a still further embodiment, the composition according to the invention is useful for enhancing mucosal barrier function.

In another embodiment, the composition is used for promoting gut health or comfort, for example, in an elderly patient.

The nutritional composition may be produced as is conventional. Consideration may be drawn to the fact that some ingredients are more difficult to dissolve in water that others and some vitamins are susceptible to heat.

For example, the fibre source, the protein source, and the lipid source may be blended, optionally passed by a kolloid mill and dissolved in water, preferably water which has been subjected to reverse osmosis, to form a liquid mixture. The temperature of the water is conveniently about 50° C. to about 80° C. to aid dispersal of the ingredients. Commercially available liquefiers may be used to form the liquid mixture. Preferably, pH of the liquid mixture is adjusted to about 6.3 to 7 with food grade hydroxids.

If used, the emulsifiers may be included in the blend. The vitamins and minerals may be added at this point but are usually added later to avoid thermal degradation. Emulsifiers and the like may be dissolved into the lipid source prior to blending. Preferably, a food grade emulsifier from a vegetable source is used. An example for a commercially obtainable food grade emulsifier is Cutina GMS V (Cognis, in France).

After preparation of a liquid mixture, heating may be stopped or the mixture may be cooled and further ingredients may be added, for example digestible carbohydrates that are easily dissolvable, such as sucrose and maltodextrins with DE of 15-25. Other easily dissolvable ingredients include, for example, oligosaccharides, vitamins, minerals, flavourings and colorants.

Preferably, pH is again adjusted at a temperature of 15-20° C. to about 6.9-7.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

In case that a liquid, shelf-stable composition is prepared, an ultra heat treatment (UHT)-treatment is preferably conducted after pre-heating to 50-85° C. For example, an indirect UHT treatment may be conducted at 140-155° C. for 5-8 s, in a tube heat exchanger, for example.

The liquid mixture may then be cooled to about 60° C. to about 85° C.; for example by flash cooling. The liquid mixture is then homogenised; for example in two stages at about 100-200 bars in the first stage and about 20-80 bars in the second stage.

For a product in liquid form, the homogenised mixture is preferably aseptically filled into suitable containers. Aseptic filling of the containers may be carried out by cooling the liquid mixture, for example in an aseptic storage tank, to a temperature of about 18 to 30° C. The homogenised mixture may then be filled into containers, for example in an $N_2$-atmosphere. Suitable apparatus for carrying out aseptic filling of this nature is commercially available.

In case a powdered, reconstitutable formula is produced, the homogenised mixture may then be further cooled to add any heat sensitive components; such as vitamins and minerals. The pH and solids content of the homogenised mixture is conveniently standardised at this point. For a product in powder form, the homogenised mixture is dried to powder; for example by spray drying. Conventional procedures may be used.

Accordingly, the process according to the present invention preferably comprises the steps of
  mixing components of the composition, and,
  hydrating the components to provide a liquid mixture.
Furthermore, the process preferably comprises the steps of
  heat treating and homogenising the liquid mixture, and, in case of a liquid composition,
  aseptically filling the composition, or, in case of a powdered and reconstitutable composition,
  drying, for example spray- or roller drying the liquid mixture to obtain the composition according to the present invention.

EXAMPLE

A ready-to-use nutritional composition is prepared. The nutritional composition includes the following components:

| Component | Conc. (/100 ml) | Total Energy (%) |
|---|---|---|
| Fibre (total) | 2.6 | |
| Soluble (acacia gum) | 0.75 g | |
| Insoluble fibre (pea outer fibre) | 1.1 g | |
| Oligosaccharides (FOS) | 0.75 g | |
| Digestible Carbohydrates (total) | 18.8 | 50 |
| Sugar | 4.8 g | |
| Maltodextrin | 13.95 g | |
| Lactose | 0.22 g | |
| Protein (total) | 5.6 g | 15 |
| Na caseinate | 2.8 g | |
| Milk protein concentrate | 2.8 g | |
| Lipids (total) | 5.85 g | 35 |
| corn oil | 2.34 g | |
| low erucic rapeseed oil | 2.13 g | |
| soy bean oil | 1.12 g | |
| milk fat | 0.09 g | |
| mono and diglycerides | 0.15 g | |
| Vitamins | | |
| Vitamin A | 420 IU | |
| Vitamin C | 15 mg | |
| Vitamin D | 60 IU | |
| Vitamin E | 2.0 mg TE | |
| Vitamin K | 8.5 µg | |
| Thiamin Vit. B1 | 0.18 mg | |
| Riboflavine Vit. B 2 | 0.195 mg | |
| Pantothenic acid | 0.75 mg | |
| Vitamin B6 | 0.255 mg | |
| Vitamin B12 | 0.55 µg | |
| Niacin | 1.8 mg | |
| Folic acid | 36 µg | |
| Biotin | 4.5 µg | |
| Minerals | | |
| Zinc, Iron, Copper, Magnesium, Manganese, Selenium, Iodine, Potassium, Calcium, Phosphorous, Chloride | 1 g | |

In a first step, acacia gum, carrageenan iota, mono- and diglycerides, lipids, pea outer fibre, protein sources, KOH and $NaH_2PO4$ were mixed in a mixer triblender, passed through a kolloid mill, and led to a holding tank where they were mixed with water and heated to 70° C. by a plate heat exchanger.

In a second step, sucrose and maltodextrin were mixed in a triblender and added to the holding tank.

In a third step, the temperature of the mixture in the holding tank was reduced to 30° C., before fructooligosaccharides (FOS), vitamins, minerals, flavours and colouring were mixed in a triblender, passed through a kolloid mill and added to the holding tank.

After stirring, the temperature of the hydrated mixture was cooled to 18° C., pH was adjusted to about 7, and dry matter was adjusted to 30%.

Thereafter, an indirect UHT was performed by preheating to 80° C., by tube heat exchanger, heating to 150° C. for 7 seconds and cooling down to 75° C. immediately.

A two stage homogenisation was conducted at 120 and 40 bar, respectively.

The temperature of the hydrated ultra heat treated and homogenised mixture was then lowered to 20° C. in a cooler, led to an aseptic storage tank and filled into 200 ml containers by aseptic filling machine.

The nutritional composition has an energy content of 1.5 kcal/ml, an osmolality of 610 mosm/kg $H_2O$ and an osmolarity of 646 mosm/kg $H_2O$.

Pea outer fibre, acacia gum and Raftilose P95™ were used as insoluble, soluble fibre and oligosaccharides, respectively.

The composition is shelf-stable for 8 months and is judged to have a good taste. Plum and vanilla were added as flavours.

The composition is rich in fibre and improves intestinal transit and improves gut flora and gut comfort.

The invention claimed is:

1. A liquid or powdered and reconstitutable nutritional composition comprising 4.5 to 6 g protein/100 ml composition, a source of digestible carbohydrates and a source of dietary fiber, having an energy density of 1.3-1.8 kcal/ml and dietary fiber in an amount of more than 2.5 g/100 ml, wherein the source of dietary fiber comprises 20-40% by weight acacia gum, 30-60% by weight of pea outer fiber and 20-40% by weight of fructooligasaccharides, wherein the composition comprises a viscosity of 30-80 mPas.

2. The composition according to claim 1 wherein the energy density is between 1.4-1.6 kcal/ml.

3. The composition according to claim 1 comprising a source of lipids.

4. The composition according to claim 1 wherein the composition is clinically free of lactose.

5. A method for improving the digestive tract and bowel function of a patient requiring same, the method comprising administering to the patient a liquid or powdered and reconstitutable nutritional composition comprising 4.5 to 6 g protein/100 ml composition, a source of digestible carbohydrates and a source of dietary fiber, having an energy density of 1.3-1.8 kcal/ml and dietary fiber in an amount of more than 2.5 g/100 ml, wherein the source of dietary fiber comprises 20-40% by weight acacia gum, 30-60% by weight of pea outer fiber and 20-40% by weight of fructooligasaccharides, wherein the composition comprises a viscosity of 30-80 mPas.

6. A method for enhancing mucosal barrier function in a patient requiring same, the method comprising administering to the patient a liquid or powdered and reconstitutable nutritional composition comprising 4.5 to 6 g protein/100 ml composition, a source of digestible carbohydrates and a source of dietary fiber, having an energy density of 1.3-1.8 kcal/ml and dietary fiber in an amount of more than 2.5 g/100 ml, wherein the source of dietary fiber comprises 20-40% by weight acacia gum, 30-60% by weight of pea outer fiber and 20-40% by weight of fructooligasaccharides, wherein the composition comprises a viscosity of 30-80 mPas.

7. A method for promoting gut health or comfort in an elderly patient in need of same, the method comprising administering to the patient a liquid or powdered and reconstitutable nutritional composition comprising 4.5 to 6 g protein/100 ml composition, a source of digestible carbohydrates and a source of dietary fiber, having an energy density of 1.3-1.8 kcal/ml and dietary fiber in an amount of more than 2.5 g/100 ml, wherein the source of dietary fiber comprises 20-40% by weight acacia gum, 30-60% by weight of pea outer fiber and 20-40% by weight of fructooligasaccharides, wherein the composition comprises a viscosity of 30-80 mPas.

8. A method for preparing a nutritional composition, the method comprising:
mixing a liquid or powdered and reconstitutable nutritional composition comprising 4.5 to 6 g protein/100 ml composition, a source of digestible carbohydrates and a source of dietary fiber, having an energy density of 1.3-1.8 kcal/ml and dietary fiber in an amount of more than 2.5 g/100 ml, wherein the source of dietary fiber comprises 20-40% by weight acacia gum, 30-60% by weight of pea outer fiber and 20-40% by weight of fructooligasaccharides, and
hydrating the components to provide a liquid mixture, wherein the composition comprises a viscosity of 30-80 mPas.

9. A method for maintaining or restoring a well-balanced gut flora, the method comprising administering to an individual in need of same a liquid or powdered and reconstitutable nutritional composition comprising 4.5 to 6 g protein/100 ml composition, a source of digestible carbohydrates and a source of dietary fiber, having an energy density of 1.3-1.8 kcal/ml and dietary fiber in an amount of more than 2.5 g/100 ml, wherein the source of dietary fiber comprises 20-40% by weight acacia gum, 30-60% by weight of pea outer fiber and 20-40% by weight of fructooligasaccharides, wherein the composition comprises a viscosity of 30-80 mPas.

10. A method for enhancing mucosal function in a human individual in need of same, the method comprising administering to the human individual a liquid or powdered and reconstitutable nutritional composition comprising 4.5 to 6 g protein/100 ml composition, a source of digestible carbohydrates and a source of dietary fiber, having an energy density of 1.3-1.8 kcal/ml and dietary fiber in an amount of more than 2.5 g/100 ml, wherein the source of dietary fiber comprises 20-40% by weight acacia gum, 30-60% by weight of pea outer fiber and 20-40% by weight of fructooligasaccharides, wherein the composition comprises a viscosity of 30-80 mPas.

* * * * *